US00PP36766P2

(12) United States Plant Patent
Schoone

(10) Patent No.: US PP36,766 P2
(45) Date of Patent: Jun. 24, 2025

(54) ***PHALAENOPSIS* PLANT NAMED 'STORYLINE'**

(50) Latin Name: *Phalaenopsis hybrida*
Varietal Denomination: Storyline

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/975,970

(22) Filed: Dec. 10, 2024

Related U.S. Application Data

(60) Provisional application No. 63/608,785, filed on Dec. 11, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Storyline', characterized by its upright plant habit; strong flowering stems; healthy and sturdy leaves; freely flowering habit with typically two inflorescences developing per plant, each inflorescence with numerous flowers; white-colored flowers with reddish purple-colored venation and random dark purplish red-colored spots; and good postproduction longevity.

2 Drawing Sheets

Figure 1:
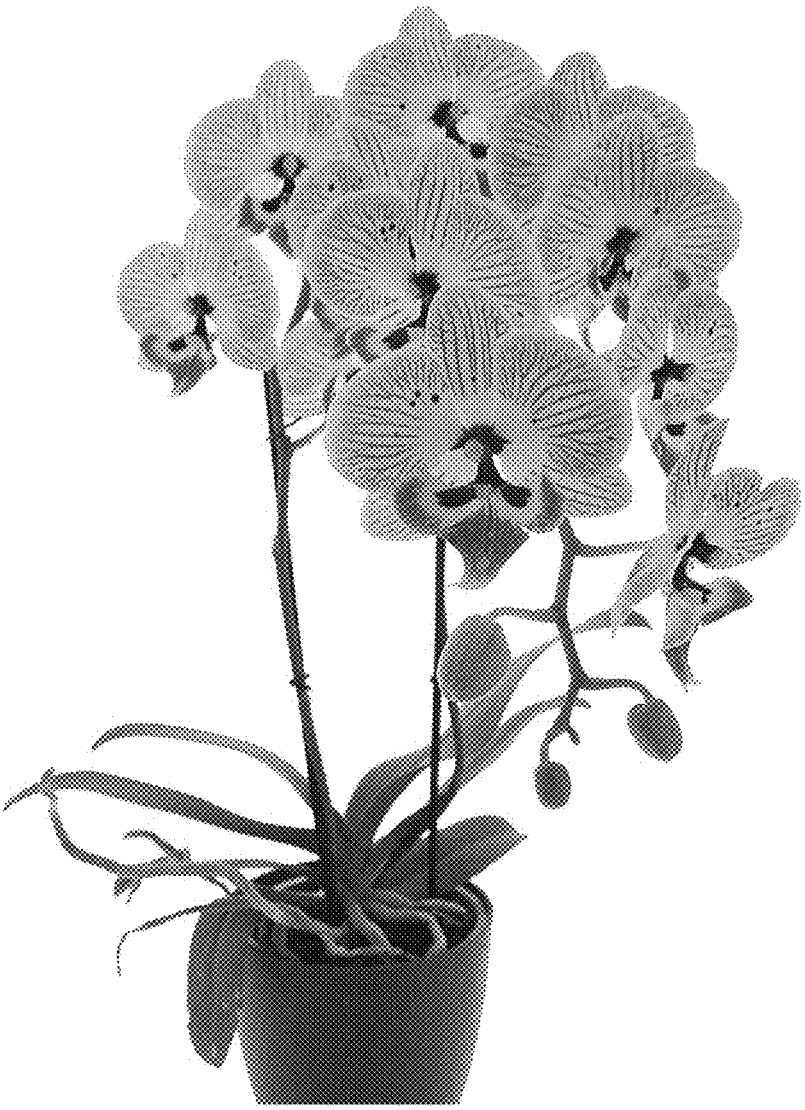

Botanical designation: *Phalaenopsis hybrida.*
Cultivar denomination: 'STORYLINE'.

CROSS-REFERENCED TO CLOSELY-RELATED APPLICATIONS

A European Community Plant Breeder's Rights application for the instant plant was filed by the Applicant/Assignee, Floricultura B.V. of Heemskerk, The Netherlands on Dec. 2, 2023, application number 2023/2628. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Storyline'.

The new *Phalaenopsis* plant is a product of a planned breeding program conducted by the Inventor in Taichung City, Taiwan, Heemskerk, The Netherlands and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in October, 2014 in Taichung City, Taiwan of *Phalaenopsis hybrida* 'Acker Sweetie', not patented, as the female, or seed, parent with *Phalaenopsis hybrida* 'Maki Watanabe', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November, 2020.

Asexual reproduction of the new *Phalaenopsis* plant by in vitro meristem propagation in a controlled environment in Assendelft, The Netherlands since November, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Storyline'. These characteristics in combination distinguish 'Storyline' as a new and distinct *Phalaenopsis* plant:

1. Upright plant habit.
2. Strong flowering stems.
3. Healthy and sturdy leaves.
4. Freely flowering habit with typically two inflorescences developing per plant, each inflorescence with numerous flowers.
5. White-colored flowers with reddish purple-colored venation and random dark purplish red-colored spots.
6. Good postproduction longevity.

Plants of the new *Phalaenopsis* can be compared to plants of the female parent, 'Acker Sweetie'. Plants of the new *Phalaenopsis* differ primarily from plants of 'Acker Sweetie' in flower color as flowers of plants of the new *Phalaenopsis* are white in color with reddish purple-colored venation with random dark purplish red-colored spots whereas flowers of plants of 'Acker Sweetie' do not have any spots. In addition, plants of the new *Phalaenopsis* are "big lip" types, that is, the central and lateral lobes of the labellum are fused, whereas plants of 'Acker Sweetie' are not "big lip" types.

Plants of the new *Phalaenopsis* can be compared to plants of the male parent, 'Maki Watanabe'. Plants of the new *Phalaenopsis* differ primarily from plants of 'Maki Watanabe' in flower shape as flowers of plants of the new *Phalaenopsis* are "big lip" types, that is, the central and lateral lobes of the labellum are fused, whereas plants of 'Maki Watanabe' are not "big lip" types.

Plants of the new *Phalaenopsis* can be compared to plants of *Phalaenopsis hybrida* 'Striped Melody', not patented. In side-by-side comparisons, plants of the new *Phalaenopsis* differ primarily from plants of 'Striped Melody' in flower color as flowers of plants of the new *Phalaenopsis* are white in color with reddish purple-colored venation with random dark purplish red-colored spots whereas flowers of plants of 'Striped Melody' do not have any spots. In addition, flowers of plants of the new *Phalaenopsis* have shorter colored veins than flowers of plants of 'Striped Melody'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Storyline' grown in a container.

Figure 2:
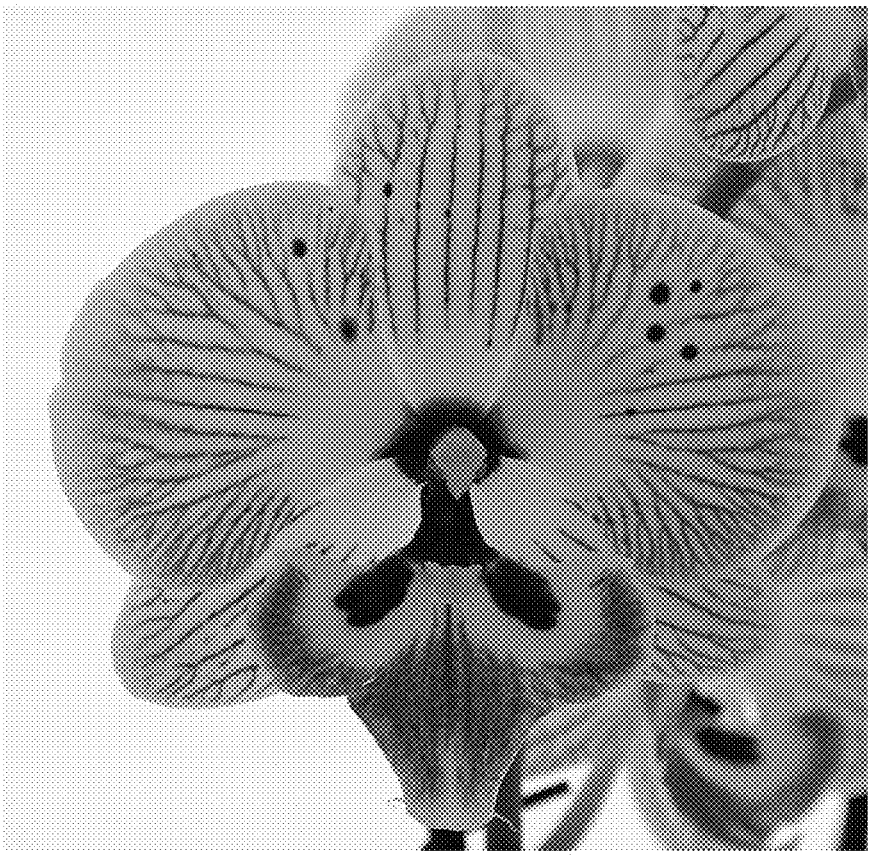

The photograph on the second sheet (FIG. 2) is a close-up view of a typical flower of 'Storyline'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Storyline'.

Parentage:

- *Female, or seed, parent.*—*Phalaenopsis hybrida* 'Acker Sweetie', not patented.
- *Male, or pollen, parent.*—*Phalaenopsis hybrida* 'Maki Watanabe', not patented.

Propagation:

- *Type.*—By in vitro meristem propagation.
- *Time to initiate roots, summer and winter.*—About two weeks at temperatures about 28° C. to 30° C.
- *Time to produce a rooted young plant, summer and winter.*—About 20 to 25 weeks at temperatures about 28° C. to 30° C.
- *Root description.*—Thin, fibrous; typically light yellowish white in color; actual color of the roots is dependent on substrate composition, water quality, fertilizer, substrate temperature and age of roots.
- *Rooting habit.*—Freely branching; medium density.

Plant description:

- *Plant form and growth habit.*—Herbaceous epiphyte; upright plant habit with typically two inflorescences developing per plant, each inflorescence with numerous flowers; monopodial; moderately vigorous growth habit and moderate growth rate.
- *Plant height, substrate level to top of foliar plane.*—About 14.8 cm.
- *Plant height, substrate level to top of floral plane.*—About 39.4 cm.
- *Plant diameter or spread.*—About 37.6 cm.

Leaf description:

- *Arrangement and quantity.*—Distichous, simple; sessile; about six to seven fully-developed leaves per plant.
- *Length.*—About 19.2 cm.
- *Width.*—About 6.3 cm.
- *Aspect.*—Erect to upwardly arching.
- *Shape.*—Oblong to narrowly obovate; slightly carinate; apex moderately recurving.
- *Apex.*—Unequal acute.
- *Base.*—Sheathing. Sheath length: About 1.8 cm. Sheath width: About 1.7 cm. Sheath color, upper and lower surfaces: Close to 143C; towards the margins, close to 143B.
- *Margin.*—Entire.
- *Texture and luster, upper and lower surfaces.*—Smooth, glabrous; slightly glossy.
- *Venation pattern.*—Camptodromous.
- *Color.*—Developing leaves, upper surface: Close to 146A with narrow marginal edges, close to 146B. Developing leaves, lower surface: Close to 146B; towards the margins, close to 146A with narrow marginal edges, close to 146B to 146C. Fully expanded leaves, upper surface: Close to 137B; venation, close to NN137B. Fully expanded leaves, lower surface: Close to 146B; towards the margins, close to a blend of 137B and 146A; venation, close to 137C.

Inflorescence description:

- *Appearance and flowering habit.*—Showy zygomorphic flowers arranged on axillary simple or branched racemes; typically two inflorescences develop per plant; each inflorescence with about 16 flowers; flowers face outwardly on outwardly arching inflorescences supported by upright peduncles; flowers with three petals, two lateral petals and one center petal transformed into a labellum and three sepals.
- *Fragrance.*—None detected.
- *Time to flower.*—Plants begin flowering about six months after planting; plants flower naturally during the winter into the spring.
- *Flower longevity and postproduction longevity.*—Long flowering period and good postproduction longevity, individual flowers maintain good substance for about 20 weeks on the plant; flowers not persistent.

*Inflorescence length* (*lowermost flower to inflorescence apex*).—About 29 cm.

*Inflorescence width*.—About 19.5 cm.

*Flower buds*.—Height: About 1.9 cm. Diameter: About 1.3 cm by 1.4 cm. Shape: Broadly ovate. Color: Close to 145A and 145B; under surface, close to 145C and 145D; venation, close to 182B.

*Flower size*.—About 7.5 cm (vertical) by 7.4 cm (horizontal).

*Flower depth*.—About 3.4 cm.

*Petals, quantity and arrangement*.—Three, two lateral petals and one center petal transformed into a labellum.

*Lateral petals*.—Length: About 3.8 cm. Width: About 4.5 cm. Shape: Broadly deltoid-reniform to roughly broadly lunate. Apex: Broad obtuse and shallowly retuse. Margin: Entire. Texture and luster, upper and lower surfaces: Smooth, glabrous; moderately velvety; matte. Color: When opening, upper surface: Ground color: Close to 155C; at the base, close to N79B. Venation: Reticulate pattern; close to a blend of N78A and NN78A; towards the margins, fading closer to a blend of N78B and NN78B. Dots: If present, typically one to six random dots per petal; about 1 mm in diameter; close to N79B and N79C in color. When opening, lower surface: Ground color: Close to 155C; at the base, close to N79B. Venation: Reticulate pattern; close to a blend of N78C and NN78C. Dots: Visible from the upper surface, typically one to six random dots per petal; close to N178B and N187C in color. Fully opened, upper surface: Ground color: Close to N155D; at the base, close to N79B. Venation: Reticulate pattern; close to N78A; towards the margins, fading closer to N78B. Dots: If present, typically one to six random dots per petal; about 1.5 mm in diameter; close to N79C in color. Fully opened, lower surface: Ground color: Close to NN155D; at the base, close to N79B. Venation: Reticulate pattern; close to N78C and N78D. Dots: Visible from the upper surface, typically one to six random dots per petal; close to N178B and N187C in color.

*Labella*.—Appearance: Roughly rhomboidal to deltoid in overall outline; apex, acute; margins, entire; slightly concave; lobes are fused to form a "big lip" type labella. Length: About 3.8 cm. Width: About 4.3 cm. Texture and luster, upper and lower surfaces: Smooth, glabrous, moderately velvety; matte. Callosities: Located at the base of the labellum and attachment point of the lateral petals; about 4 mm in length, about 5 mm in width and about 5 mm in height. Color: When opening, upper surface: Ground color: Close to NN155D; lower margins, tinged with close to 1D; at the base, close to 187A. Venation: Midvein, close to NN78A and towards the apex and margins, closer to a blend of 84D and NN155D; lateral venation, close to N78A and N78B. When opening, lower surface: Ground color: Close to 155C; fading towards the base to closer to 157D and at the base, close to N187C. Venation: Close to N78C and N78D. Fully opened, upper surface: Ground color: Close to NN155D; at the base, close to 187A. Venation: Midvein, close to N78A; lateral venation, close to N78B. Fully opened, lower surface: Ground color: Close to NN155C; at the base, close to N187C. Venation: Close to N78C and N78D. Callosities: When developing: Close to 155C; towards the apex, tinged with close to 184A, 1B and 1C. Fully developed: Close to NN155D; towards the apex, tinged with close to N79B, 4B and 4C.

*Sepals*.—Quantity and arrangement: Three, one upper dorsal sepal and two lower lateral sepals. Length, dorsal sepal: About 3.9 cm. Width, dorsal sepal: About 2.7 cm. Length, lateral sepals: About 3.9 cm. Width, lateral sepals: About 2.5 cm. Shape, dorsal sepal: Ovate-elliptic to elliptic. Shape, lateral sepals: Ovate. Apex, dorsal sepal: Obtuse to shallowly retuse. Apex, lateral sepals: Bluntly acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Ground color: Close to 155C; at the base, close to N79B. Venation: Reticulate pattern; close to a blend of N78A and NN78A. Dots: If present, typically one to four random dots per petal; about 0.75 mm in diameter; close to N79B in color. When opening, lower surface: Ground color: Close to 145D; towards the margins, close to N155B. Venation: Reticulate pattern; close to 186C and 186D. Fully opened, upper surface: Ground color: Close to NN155D; at the base, close to 77A. Venation: Reticulate pattern; close to N78A; towards the margins, fading to closer to N78B. Dots: If present, typically one to four random dots per petal; about 1 mm in diameter; close to N79C in color. Fully opened, lower surface: Ground color: Close to NN155D; at the base, close to N79B. Venation: Reticulate pattern; close to N78D. Color, lateral sepals: When opening, upper surface: Ground color: Close to 155C; towards the base, close to 157B and at the base, close to N79B. Venation: Reticulate pattern; close to a blend of N78A and NN78A. When opening, lower surface: Ground color: Close to 145C and 145D; towards the margins, close to N155B. Venation: Midvein, close to 145A; reticulate lateral venation, close to 186C and 186D. Fully opened, upper surface: Ground color: Close to NN155D; at the base, close to N79B. Venation: Reticulate pattern; close to N78A; towards the margins, fading to closer to N78B. Fully opened, lower surface: Ground color: Close to NN155D; at the base, close to N79B. Venation: Reticulate pattern; close to N78D.

*Peduncles*.—Length: About 51.9 cm. Diameter: About 4.5 mm. Strength: Strong. Aspect: Upright to outwardly arching. Texture and luster: Smooth, glabrous; matte. Color: Close to 138A densely covered with fine dots, close to 145B.

*Pedicels*.—Length: About 4 cm. Diameter: About 3 mm. Strength: Moderately strong. Aspect: About 50° from peduncle axis. Texture and luster: Smooth, glabrous; matte. Color: Close to 144B; distal end, close to 155C.

*Reproductive organs*.—Androecium: Column length: About 8 mm. Column width: About 5.5 mm. Column color: Close to N78A; towards the apex, close to NN155A. Pollinia quantity: Two. Pollinia diameter (per two pollinia): About 3 mm. Pollinia color: Close to 23A. Gynoecium: Stigma length: About 3 mm.

Stigma width: About 4 mm. Stigma shape: Reniform. Stigma color: Close to N155A; marginal edges, close to N78A. Ovary length: About 8 mm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Storyline' as herein illustrated and described.

* * * * *